(12) United States Patent
Raby et al.

(10) Patent No.: US 7,613,527 B2
(45) Date of Patent: Nov. 3, 2009

(54) ORTHODONTIC PRESCRIPTION FORM, TEMPLATES, AND TOOLBAR FOR DIGITAL ORTHODONTICS

(75) Inventors: Richard E. Raby, North St. Paul, MN (US); Nicholas A. Stark, Cottage Grove, MN (US); Peter M. Eisenberg, Minneapolis, MN (US); Theresa M. Meyer, Osceola, WI (US)

(73) Assignee: 3M Innovative Properties Company, Saint Paul, MN (US)

( * ) Notice: Subject to any disclaimer, the term of this patent is extended or adjusted under 35 U.S.C. 154(b) by 197 days.

(21) Appl. No.: 11/670,466

(22) Filed: Feb. 2, 2007

(65) Prior Publication Data

US 2007/0218418 A1    Sep. 20, 2007

Related U.S. Application Data

(60) Provisional application No. 60/782,919, filed on Mar. 16, 2006.

(51) Int. Cl.
*G06F 3/00* (2006.01)
*G05B 11/01* (2006.01)
*G05B 15/00* (2006.01)
*A61C 3/00* (2006.01)
*G06F 17/50* (2006.01)

(52) U.S. Cl. ............... 700/17; 700/83; 715/700; 433/2; 433/24; 703/1

(58) Field of Classification Search ........... 433/24, 433/2; 703/1; 700/17, 83; 715/700
See application file for complete search history.

(56) References Cited

U.S. PATENT DOCUMENTS 3,861,044 A   1/1975  Swinson, Jr.
4,204,325 A   5/1980  Kaelble
4,528,627 A   7/1985  Coben
4,611,288 A   9/1986  Duret et al.
4,668,192 A   5/1987  Lavin (Continued)

FOREIGN PATENT DOCUMENTS

CA    2292141    6/2001

(Continued)

OTHER PUBLICATIONS

"The Orthos Approach . . . The First Comprehensive Appliance System Designed to Address Common Clinical Problems," Product literature of Ormco Company, 7 pages (undated).

(Continued)

*Primary Examiner*—Ronald D Hartman, Jr.
(74) *Attorney, Agent, or Firm*—Lance L. Vietzke (57) ABSTRACT

Computer-based techniques are described that use orthodontic prescription templates to assist an orthodontic practitioner in creating a patient-specific orthodontic prescription. In particular, an orthodontic practitioner may retrieve a stored electronic orthodontic prescription template. The practitioner may then generate an orthodontic prescription that is specific to a patient's teeth by modifying one or more bracket attributes of the template within orthodontic modeling software. Subsequently, the practitioner may communicate the patient-specific orthodontic prescription to a manufacturing facility that constructs an indirect bonding tray for use in physically placing brackets on the patient's teeth.

25 Claims, 12 Drawing Sheets

U.S. PATENT DOCUMENTS

| | | | |
|---|---|---|---|
| 4,742,464 A | 5/1988 | Duret et al. | |
| 4,837,732 A | 6/1989 | Brandestini et al. | |
| 4,919,615 A | 4/1990 | Croll | |
| 4,964,770 A | 10/1990 | Steinbichler et al. | |
| 5,011,405 A | 4/1991 | Lemchen | |
| 5,027,281 A | 6/1991 | Rekow et al. | |
| 5,028,232 A | 7/1991 | Snow | |
| 5,078,599 A | 1/1992 | Eenboom et al. | |
| 5,131,844 A | 7/1992 | Marinaccio et al. | |
| 5,139,419 A | 8/1992 | Andreiko et al. | |
| 5,212,871 A | 5/1993 | Luccarelli | |
| 5,237,998 A | 8/1993 | Duret et al. | |
| 5,266,030 A | 11/1993 | Van Der Zel | |
| 5,278,756 A | 1/1994 | Lemchen et al. | |
| 5,322,436 A | 6/1994 | Horng et al. | |
| 5,338,198 A | 8/1994 | Wu et al. | |
| 5,342,194 A | 8/1994 | Feldman | |
| 5,354,199 A | 10/1994 | Jacobs et al. | |
| 5,368,478 A | 11/1994 | Andreiko et al. | |
| 5,372,502 A | 12/1994 | Massen et al. | |
| 5,395,238 A | 3/1995 | Andreiko et al. | |
| 5,417,572 A | 5/1995 | Kawai et al. | |
| 5,454,717 A | 10/1995 | Andreiko et al. | |
| RE35,169 E | 3/1996 | Lemchen et al. | |
| 5,518,397 A | 5/1996 | Andreiko et al. | |
| 5,533,895 A | 7/1996 | Andreiko et al. | |
| 5,538,129 A | 7/1996 | Chester et al. | |
| 5,575,645 A | 11/1996 | Jacobs et al. | |
| 5,605,459 A | 2/1997 | Kuroda et al. | |
| 5,674,069 A | 10/1997 | Osorio | |
| 5,683,243 A | 11/1997 | Andreiko et al. | |
| 5,851,115 A | 12/1998 | Carlsson et al. | |
| 5,879,158 A | 3/1999 | Doyle et al. | |
| 5,882,192 A | 3/1999 | Bergersen | |
| 5,975,893 A | 11/1999 | Chishti et al. | |
| 6,068,482 A | 5/2000 | Snow | |
| 6,089,868 A | 7/2000 | Jordan et al. | |
| 6,152,731 A | 11/2000 | Jordan et al. | |
| 6,227,850 B1 | 5/2001 | Chishti et al. | |
| 6,244,861 B1 | 6/2001 | Andreiko et al. | |
| 6,250,918 B1 | 6/2001 | Sachdeva et al. | |
| 6,309,215 B1 | 10/2001 | Phan et al. | |
| 6,315,553 B1 | 11/2001 | Sachdeva et al. | |
| 6,318,994 B1 | 11/2001 | Chishti et al. | |
| 6,350,119 B1 | 2/2002 | Jordan et al. | |
| 6,350,120 B1 | 2/2002 | Sachdeva et al. | |
| 6,616,444 B2 | 9/2003 | Andreiko et al. | |
| 6,632,089 B2 | 10/2003 | Rubbert et al. | |
| 6,664,986 B1 | 12/2003 | Kopelman et al. | |
| 6,733,289 B2 * | 5/2004 | Manemann et al. | 433/24 |
| 6,776,614 B2 * | 8/2004 | Wiechmann et al. | 433/24 |
| 6,971,873 B2 * | 12/2005 | Sachdeva et al. | 433/24 |
| 7,074,039 B2 * | 7/2006 | Kopelman et al. | 433/24 |
| 7,155,373 B2 * | 12/2006 | Jordan et al. | 703/1 |
| 2001/0002310 A1 | 5/2001 | Chishti et al. | |
| 2002/0015934 A1 | 2/2002 | Rubbert et al. | |
| 2003/0027098 A1 * | 2/2003 | Manemann et al. | 433/24 |
| 2003/0163291 A1 | 8/2003 | Jordan et al. | |

FOREIGN PATENT DOCUMENTS

| | | |
|---|---|---|
| DE | 38 10 455 | 10/1989 |
| DE | 196 51 223 | 6/1998 |
| EP | 0 502 227 | 9/1992 |
| EP | 0 634 150 | 1/1995 |
| EP | 0696444 | 2/1996 |
| EP | 0595231 | 4/1997 |
| IL | 114691 | 7/1995 |
| IL | 118523 | 5/1996 |
| IL | 120867 | 5/1997 |
| IL | 120892 | 5/1997 |
| IL | 121872 | 9/1997 |
| WO | WO 90/08512 | 8/1990 |
| WO | WO 96/28112 | 9/1996 |
| WO | WO 97/03622 | 2/1997 |
| WO | WO 99/16380 | 4/1999 |
| WO | WO 99/34747 | 7/1999 |
| WO | WO 00/19931 | 4/2000 |
| WO | WO 01/80765 | 11/2001 |
| WO | WO 01/82192 | 11/2001 |
| WO | WO 01/85047 | 11/2001 |
| WO | WO 01/87179 | 11/2001 |

OTHER PUBLICATIONS

"Biomechanics in Orthodontics," Product literature of Giorgio Fiorelli—Birte Melsen, 2 pages (undated).

T. Kuroda et al., "Three-dimensional dental cast analyzing system using laser scanning", J. Am. Ortho. Dent. Orthop., 110, 365-369 (Oct. 1996).

D. Laurendeau et al., "A Computer-Vision Technique for the Acquisition and Processing of 3-D Profiles of Dental Imprints: An Application I Orthodontics", IEEE Transactions on Medical Imaging, 10, 453-461 (Sep. 1991).

Mortenson, Michael E. "Geometric Modeling", 1985, John Wiley & Sons.

* cited by examiner

ORTHODONTIC PRESCRIPTION FORM, TEMPLATES, AND TOOLBAR FOR DIGITAL ORTHODONTICS

This application claims the benefit of U.S. Provisional Application No. 60/782,919, filed Mar. 16, 2006, the entire content of which is incorporated herein by reference.

TECHNICAL FIELD

The invention relates to computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances, known as brackets, that are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly from one appliance to the next in accordance with the patient's malocclusions. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

As can be appreciated, it is important for the practitioner using straight wire appliances to fix each bracket in the exact proper position on the corresponding tooth. If, for example, a bracket is placed too far in an occlusal direction on the tooth surface, the archwire will tend to position the crown of the tooth too close to the gingiva (gums) at the end of the treatment. As another example, if the bracket is placed to one side of the center of the tooth in either the mesial or distal directions, the resultant tooth orientation will likely be an orientation that is excessively rotated about its long axis.

The process of positioning and bonding the brackets to the patient's teeth requires considerable care, and requires the practitioner to visually determine the proper location of the brackets on the respective teeth. Often, a practitioner determines bracket positions by the use of a ruler, protractor and pencil to measure and mark features on a plaster cast made from impressions of the patient's teeth. This process is often difficult to carry out with precision, and may be subjective in nature. Consequently, it is often difficult for the practitioner to ensure that the brackets are precisely positioned on the teeth at correct locations.

SUMMARY

In general, the invention relates to techniques for assisting practitioners in orthodontic diagnosis and treatment. More specifically, a system is described that provides an environment for modeling and depicting a three-dimensional (3D) representation of a patient's dental arch. By interacting with the system, orthodontic practitioners are able to visualize the 3D representation of the dental arch, and precisely position "virtual" orthodontic appliances relative to the modeled dental arch. Further, the system allows orthodontic practitioners to use and create orthodontic prescription templates that may be modified to create orthodontic prescriptions for individual patients. For example, the orthodontic practitioner may interact with the system to position brackets on one or more teeth within the modeled dental arch based on an orthodontic prescription template.

In one embodiment, the invention is directed to a method comprising retrieving a saved electronic orthodontic prescription template and generating an orthodontic prescription that is specific to a patient's teeth by modifying the template within orthodontic modeling software. The method also includes communicating the patient-specific orthodontic prescription to a manufacturing facility that constructs an indirect bonding tray for use in physically placing brackets on the patient's teeth.

In another embodiment, the invention is directed to a computing device comprising a database to store an electronic orthodontic prescription template and a modeling software module to facilitate generation of an orthodontic prescription that is specific to a patient's teeth by modifying the template. The computing device also comprises a network interface to communicate the patient-specific orthodontic prescription to a manufacturing facility that constructs an indirect bonding tray for use in physically placing brackets on the patient's teeth.

In another embodiment, the invention is directed to a computer-readable medium containing instructions. The instructions cause a programmable processor to retrieve a saved electronic orthodontic prescription template and to generate an orthodontic prescription that is specific to a patient's teeth by modifying the template within orthodontic modeling software. The instructions also cause the processor to communicate the patient-specific orthodontic prescription to a manufacturing facility that constructs an indirect bonding tray for use in physically placing brackets on the patient's teeth.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 3A is a display diagram illustrating an exemplary template editing form for defining and editing an orthodontic prescription template within modeling software.

FIG. 3B is a display diagram illustrating an exemplary bracket selection dialog form.

FIG. 11 is a display diagram in which an exemplary prescription form using a tooth chart with columnar bracket attributes similar to the template editing form of FIG. 3A.

DETAILED DESCRIPTION

Figure 1:
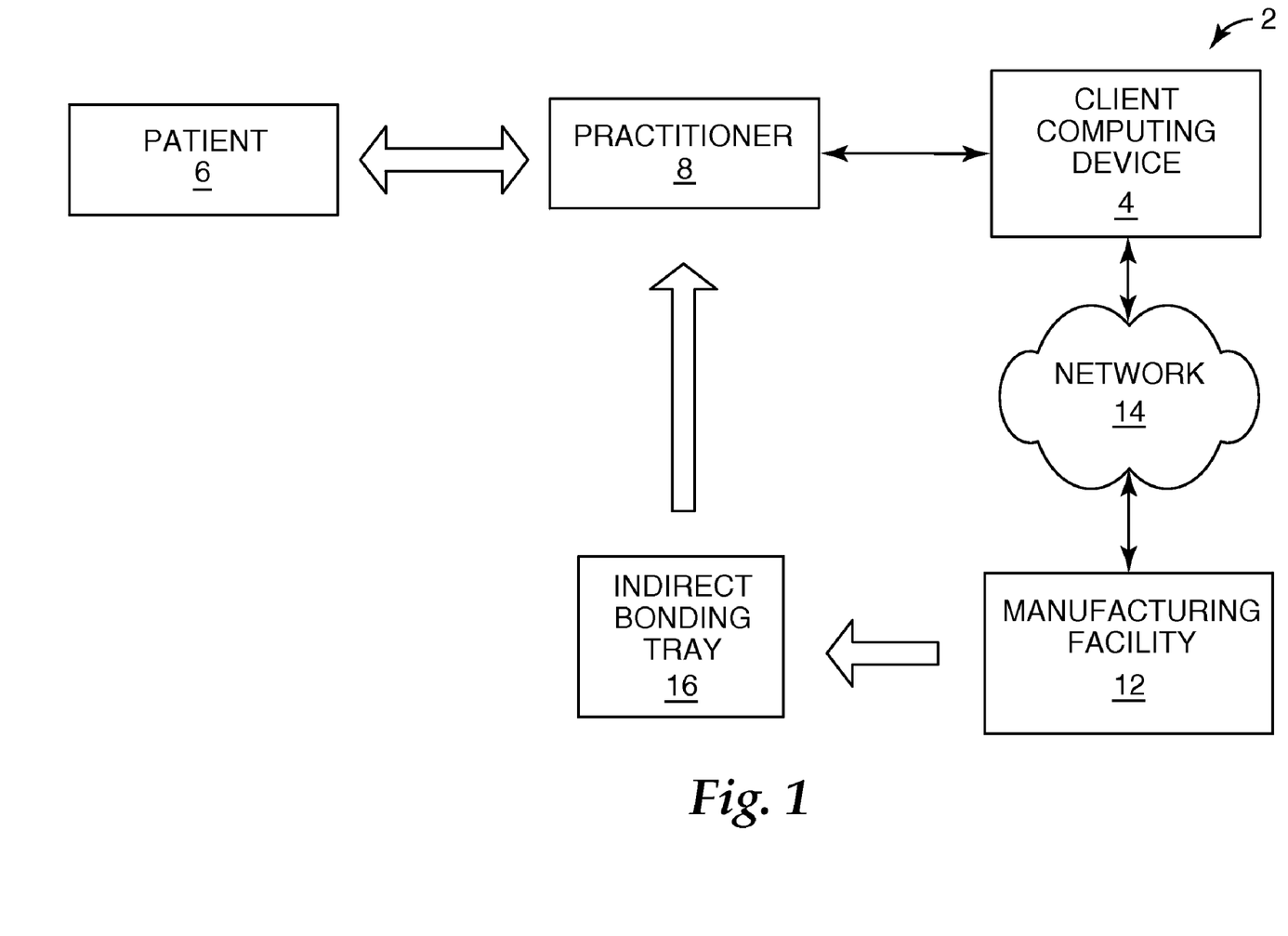
FIG. 1 is a block diagram illustrating an exemplary digital orthodontics system in which a client computing device presents an environment for modeling a representation of a dental arch of patient.

FIG. 1 is a block diagram illustrating an exemplary digital orthodontics system 2 in which a client computing device 4 presents an environment for modeling a representation of a dental arch of a patient 6. An orthodontic practitioner 8 interacts with modeling software executing on client computing device 4 to visualize the 3D representation of the dental arch, and precisely position "virtual" brackets on individual teeth within the modeled dental arch.

In this manner, the orthodontic practitioner interacts with the modeling software to digitally develop a digital orthodontic prescription. The digital orthodontic prescription, which may be abbreviated Rx, is comprised of a set of orthodontic appliances (e.g., brackets) having a set of attributes and associated with the teeth in the patient's digital dentition.

As described herein, client computing device 4 allows practitioner 8 to digitally define and manage digital prescription templates from which to specify digital prescriptions. For example, in some situations, orthodontic practitioner 8 may be able to treat a large percentage of cases with the same orthodontic prescription and still achieve the desired functional and aesthetic results in the patient's occlusion. In some cases, orthodontic practitioner 8 may wish to develop digital prescriptions based on conventional (non-computer-based) prescriptions that have been designed by certain experts in the field and are sometimes called "standard prescriptions." Since each bracket type may differ in its geometric design, a standard prescription may differ somewhat between bracket types if there is not also standardization among attributes of bracket geometry.

Moreover, orthodontic practitioner 8 may wish to create his or her own "standard prescriptions" that express their own functional and aesthetic ideals. Practitioner 8 may exercise his or her standard prescriptions on many of their own patients without ever publishing the specifics or otherwise sharing such specifics with other practitioners.

Orthodontic practitioner 8 may desire a custom digital prescription in any case when the functional or aesthetic requirements of patient 6 deviate sufficiently from the norm for which a standard prescription was designed. In this case, orthodontic practitioner 8 may create a customized digital prescription either by starting with a digital representation of a standard orthodontic prescription and making changes to one or more virtual representations of the brackets or by individually selecting a bracket for each tooth based on specific bracket attributes. Typical bracket attributes include type, slot size, torque, angulation, in/out, mesio-distal width, hook, headgear, buccal length, and distal offset. Bracket attributes may also include identification of the materials used to make the bracket, such as stainless steel, ceramic or plastic. Optionally, bracket attributes may include identification of the brackets by brand name or by the name of the vendor or manufacturer. For any given tooth, vendors offer brackets that represent several, possibly many permutations of the values that its attributes can attain. Vendors may offer thousands of distinct brackets in their product catalogs. When practitioner 8 varies brackets across the entire dentition, almost countless custom prescriptions are possible.

This variety may pose certain challenges to a practitioner, such as practitioner 8, who wishes to inventory a variety of brackets and select among them when customizing prescriptions. The use of virtual treatment planning (and appliance selection) software, coupled with an automated manufacturing system for the production of indirect bonding trays, may have certain advantages over current methods of maintaining inventories and handling appliances for custom prescriptions. Most notably, brackets may be quickly identified by a set of attributes listed in a Graphical User Interface (GUI), rather than searching through a product catalog to identify a bracket by product ID and subsequently looking for that product ID on a drawer in a large parts box.

In one embodiment, practitioner 8 interacts with digital orthodontics system 2 to create the digital prescription by adjusting a selected template as needed to ultimately specify the type of bracket for each tooth and the position and orientation of each bracket. During this process, practitioner 8 may indicate which teeth are missing from a particular patient, which teeth will be extracted, and which teeth will not have a bracket placed. Together, this information comprises a prescription (in the context of a digital orthodontics system). Recognizing that most orthodontic practitioners use a similar set of brackets and prefer a similar set of bracket heights across a wide range of patients, it may be inefficient for the orthodontic practitioners to have to specify every attribute of a prescription, from scratch, on a prescription form for each patient. With digital orthodontics system 2, it is possible to provide digital representations (i.e., templates) of standard orthodontic prescriptions to use as a starting point for each patient, as long as the orthodontic practitioner may modify the information to account for individual patient characteristics. Each orthodontic prescription template defines one or more default orthodontic appliances associated with teeth of a generic dental arch, and may specify default locations and orientations of the appliances.

Further, many practitioners use several standard prescriptions. For these and many other practitioners, standard prescriptions may not be exactly what they would really like to have as a starting point for a prescription. For this reason, software on client computing device 4 allows practitioner 8 to set up custom "starting point" prescriptions, which are referred to herein as custom orthodontic prescription templates or merely custom templates.

Subsequently, practitioner 8 may use a template to create a patient-specific orthodontic prescription. For instance, software on client computing device 4 allows practitioner 8 to modify one or more bracket attribute values in prescription templates to generate orthodontic prescriptions that meet requirements of individual patients.

Once practitioner 8 has modified the bracket attributes of a prescription template to suit patient 6, client computing device 4 may communicate the bracket attributes to manufacturing facility 12 via network 14. In response, manufacturing facility 12 constructs an indirect bonding tray 16 for use in physically placing brackets on the teeth of patient 6. In other words, manufacturing facility 12 fabricates indirect bonding tray 16 based on the bracket placement positions selected by practitioner 8 within the 3D environment presented by client computing device 4. Manufacturing facility 12 may, for example, use conventional commercially-available brackets selected by practitioner 8 to form indirect bonding tray 16. Manufacturing facility 12 forwards indirect bonding tray 16 to practitioner 8 for use in a conventional indirect bonding procedure to place the brackets on the teeth of patient 6.

Alternatively, client computing device 4 need not forward the bracket placement positions to manufacturing facility 12. Client computing device 4 may instead output, e.g., display or print, the relevant distances and angles for each bracket to assist practitioner 8 in manually positioning the brackets on the teeth of patient 6.

Figure 2:
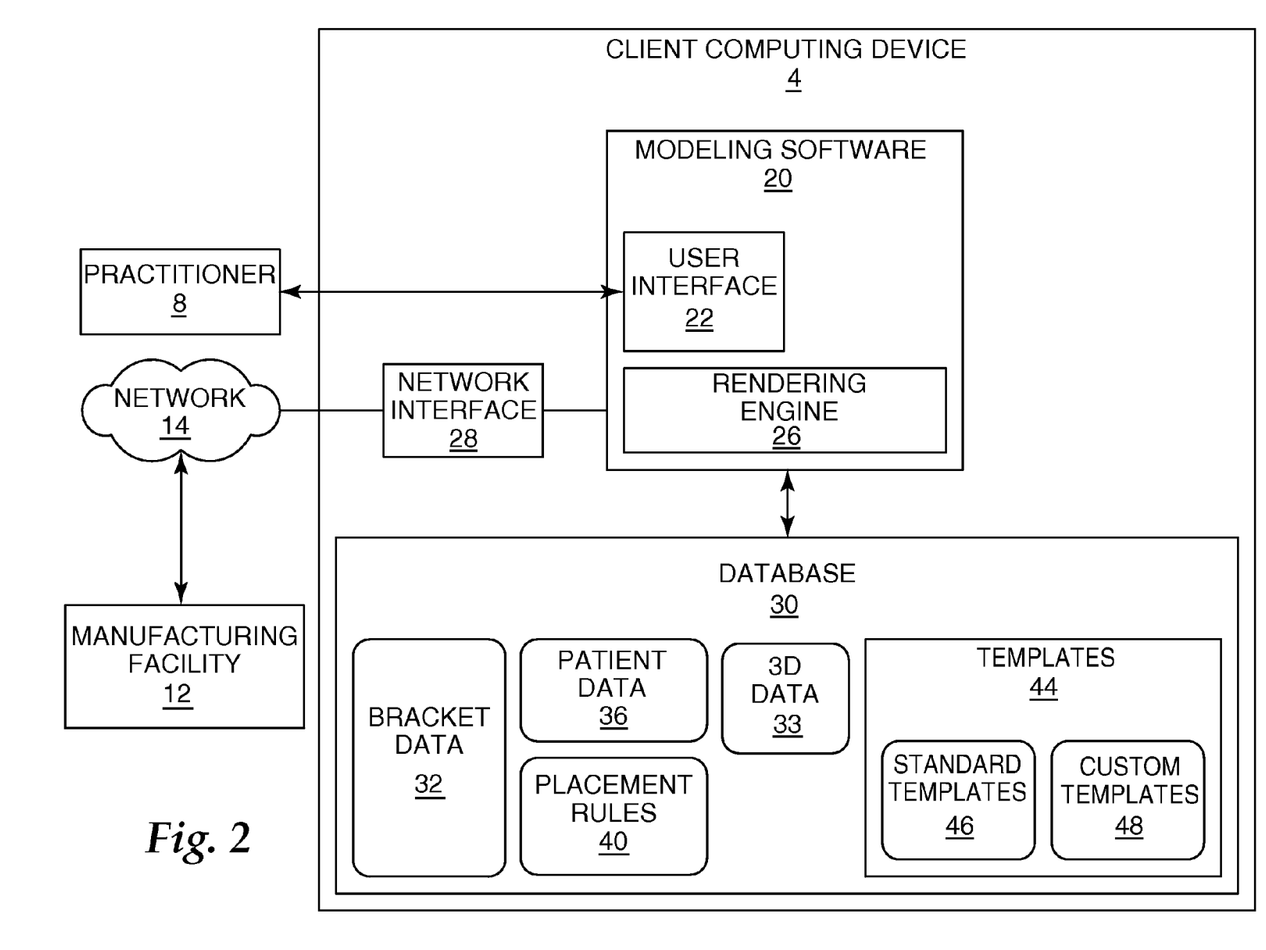
FIG. 2 is a block diagram illustrating an example embodiment of the client computing device of FIG. 1 in further detail.

FIG. 2 is a block diagram illustrating an example embodiment of client computing device 4 in further detail. In the illustrated embodiment, client computing device 4 provides an operating environment for modeling software 20. Modeling software 20 presents a modeling environment for modeling and depicting the representation of the teeth of patient 6 (FIG. 1). In the illustrated embodiment, modeling software 20 includes a practitioner interface 22 and a rendering engine 26.

Practitioner interface 22 provides a graphical user interface (GUI) that visually displays a representation of the patient's teeth, as well as representations of the brackets. In addition, practitioner user interface 22 presents an interface for receiving input from practitioner 8, e.g., via a keyboard and a pointing device, for manipulating the brackets and placing the brackets on respective teeth within the modeled dental arch.

Modeling software 20 interacts with database 30 to access a variety of data, such as bracket data 32, patient data 36, and placement rules 40. Database 30 may be represented in a variety of forms including data storage files, lookup tables, or a database management system (DBMS) executing on one or more database servers. The database management system may be a relational (RDBMS), hierarchical (HDBMS), multidimensional (MDBMS), object oriented (ODBMS or OODBMS) or object relational (ORDBMS) database management system. The data may, for example, be stored within a single relational database such as SQL Server from Microsoft Corporation. Although illustrated as local to client computing device 4, database 30 may be located remote from the client computing device and coupled to the client computing device via a public or private network, e.g., network 14.

Bracket data 32 describes a set of commercially-available brackets that practitioner 8 may select and position within the modeling environment. For example, bracket data 32 may store a variety of attributes for the commercially-available brackets, such as dimensions, slot locations and characteristics, torque angles, angulations and other attributes. Practitioner interface 22 provides a menu-driven interface by which practitioner 8 selects the type of brackets for use in defining a prescription for patient 6.

Patient data 36 describes a set of one or more patients, e.g., patient 6, associated with practitioner 8. For example, patient data 36 specifies general information, such as a name, birth date, and a dental history, for each patient. In addition, patient data 36 specifies a current prescription for each patient, including the types of brackets selected by practitioner 8 for use with each patient.

In addition, database 30 includes data defining a set of orthodontic prescription templates 44. Each of orthodontic prescription templates 44 provides default orthodontic prescription information. For example, an orthodontic prescription template may provide a default bracket type, a slot size, torque, angulation, and so on for each tooth. Templates 44 may include templates for a general orthodontic condition. For instance, templates 44 may include one template for correcting a deep overbite between two teeth and another template for correcting a canted smile. Thus, instead of specifying every element of a prescription for patient 6, practitioner 8 may select an orthodontic prescription template from templates 44 as a starting point.

Templates 44 may be provided with modeling software 20 on installation or may be imported into modeling software 20 from a vendor of modeling software 20 or from other practitioners. Modeling software 20 may also include an export function to enable practitioner 8 to save a template and send the template to someone else for import into another copy of modeling software 20.

To use one of templates 44, practitioner 8 retrieves one of templates 44. For example, practitioner 8 may retrieve a template from a set of standard templates 46 in set of templates 44. Standard templates 46 may describe generalized orthodontic prescriptions used widely within the community of orthodontic practitioners. A vendor may include standard templates 46 with modeling software 20. Alternatively, practitioner 8 may retrieve a template from a set of custom templates 48 in set of templates 44. Custom templates 48 may describe generalized orthodontic prescriptions that meet the aesthetic or clinical preferences of practitioner 8. Practitioner 8 may modify information in one of standard templates 46 to create a custom template or may create a custom template from scratch.

After retrieving one of templates 44, practitioner 8 may use the retrieved template to create an orthodontic prescription that is specific to patient 6. For instance, practitioner 8 may edit one or more values in the retrieved template to suit the specific needs of patient 6. By using a template, practitioner 8 need not specify all of the values of a patient-specific orthodontic prescription for each patient. Rather, practitioner 8 may create a patient-specific orthodontic prescription by updating a relatively smaller number of values in a generalized template.

When practitioner 8 has finished creating a patient-specific orthodontic prescription based on a template, practitioner 8 may communicate the prescription to manufacturing facility 12. Subsequently, manufacturing facility 12 constructs an indirect bonding tray for use in physically placing brackets on the teeth of patient 6.

In some embodiments, templates 44 may have ownership attributes. The ownership attributes of a template allow the template to be associated with a particular orthodontic practitioner. In addition, practitioners may use template ownership attributes to limit viewing, editing, and use rights of templates. For example, if the ownership attributes specify that a template is associated with Dr. Cook, client computing device 4 may prevent Dr. Herbert from editing the template without Dr. Cook's permission.

Modeling software 20 may display a template editing form for templates 44 according to several template editing forms. For instance, one template editing form may display a tooth chart with columnar bracket attributes. A second template editing form may display template information in a stacked quadrant format with arch graphics and row-based bracket attributes. Another template editing form may display template information in a graphical tooth chart.

When practitioner 8 is creating a patient-specific orthodontic prescription, modeling software 20 may display a prescription form in a similar way as the template editing forms. For example, modeling software 20 may display a prescription form as a tooth chart with columnar bracket attributes. In addition, a prescription form may provide tool-tip information to allow easy browsing through bracket attributes. A prescription form may also provide additional features. For example, a prescription form may allow practitioner 8 to indicate whether patient 6 is missing a tooth or whether practitioner 8 is planning on extracting a tooth before attaching brackets.

FIG. 3A is a display diagram illustrating an exemplary template editing form 50 for creating and managing an orthodontic prescription template 52 within modeling software 20 (FIG. 2). In the illustrated exemplary embodiment, template editing form 50 arranges all of the bracket attribute information of template 52 for each tooth in groups of eight teeth (upper left quadrant, upper right, lower left, lower right). Practitioner 8 may click on the column of information for each tooth to select a tooth. When practitioner 8 clicks on a "Change Bracket" button of template editing form 50, modeling software 20 opens a bracket selection dialog.

FIG. 3B is a display diagram illustrating an exemplary bracket selection dialog 60. Modeling software 20 may open bracket selection dialog 60 when practitioner 8 clicks on the "Change Bracket" button of template editing form 50 (FIG. 3A). Bracket selection dialog 60 shows attributes of a selected bracket in the column on the left and all of the appropriate bracket choices for the selected tooth, one bracket per column, in a scrollable list on the right. By changing the values in bracket selection dialog 60, practitioner 8 may change the bracket attributes in, for example, template 52.

Figure 4:
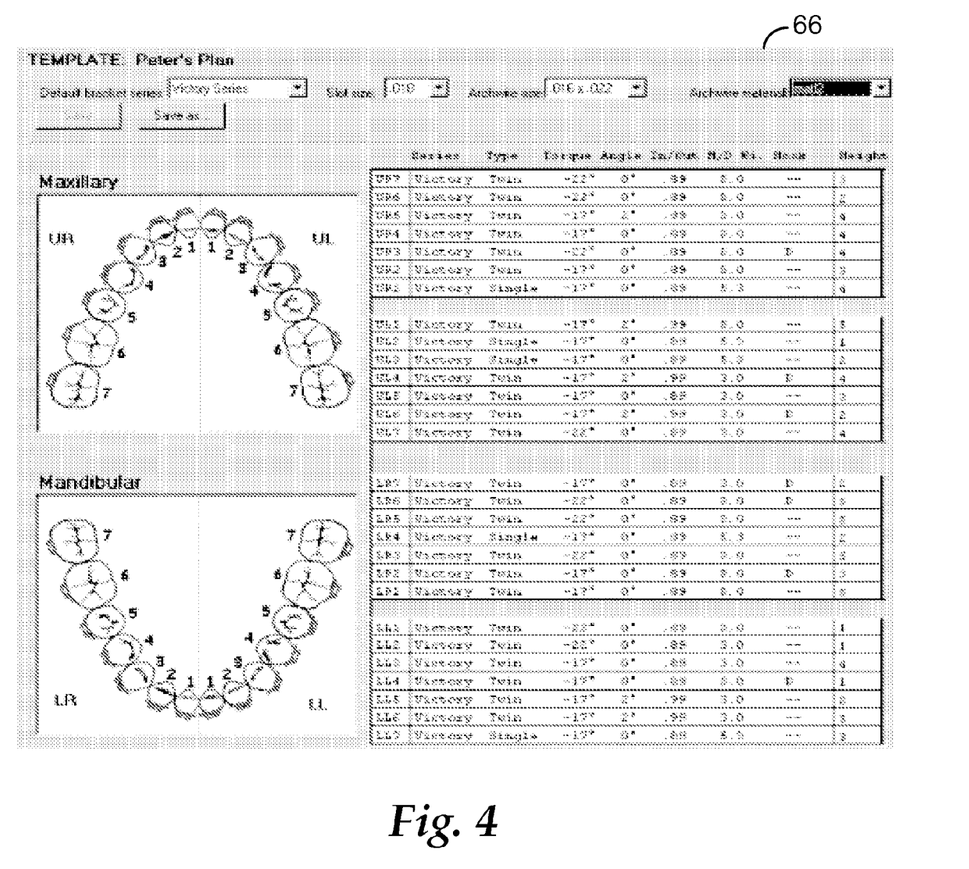
FIG. 4 is a display diagram illustrating an exemplary template editing form for creating and managing an orthodontic template that arranges orthodontic prescription template information in a stacked quadrant format with arch graphics and row-based bracket attributes.

FIG. 4 is a display diagram illustrating an exemplary template editing form 66 for creating and managing an orthodontic template that arranges orthodontic prescription template information in a stacked quadrant format with arch graphics and row-based bracket attributes. Template editing form 66 presents bracket information for each tooth in a horizontal row. Template editing form 66 also indicates information about the tooth/bracket graphically.

Figure 5A:
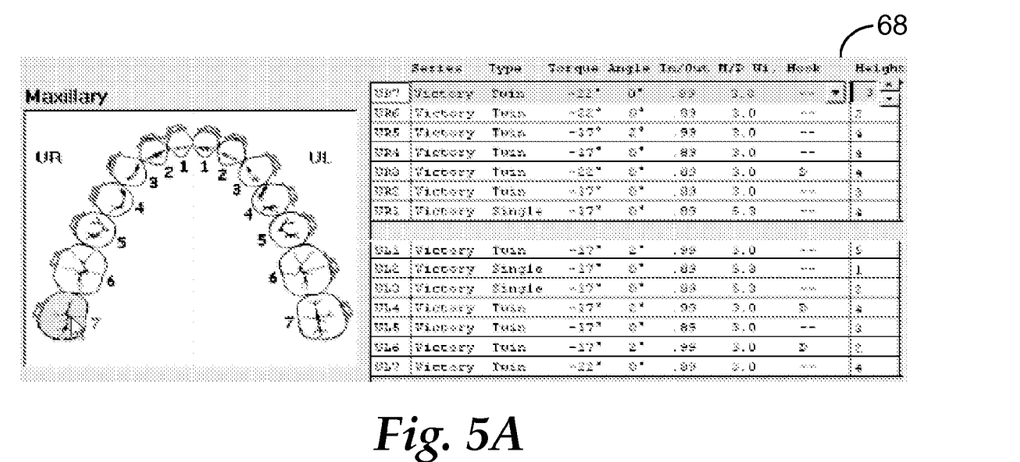
FIG. 5A is a display diagram illustrating an exemplary view when a practitioner selects a tooth on the graphic or in the table of the template editing form of FIG. 4.

FIG. 5A is a display diagram illustrating an exemplary view 68 when practitioner 8 selects a tooth on the graphic or in the table of template editing form 66 (FIG. 4). As shown in FIG. 5A, modeling software 20 highlights the tooth and the corresponding row of bracket attributes when practitioner 8 clicks on a specific tooth in the graphical representation of a dental arch.

Figure 5B:
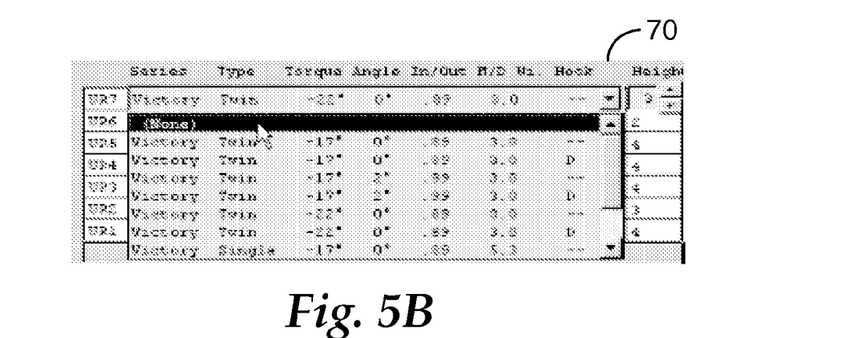
FIG. 5B is a display diagram illustrating an exemplary view that demonstrates how a practitioner edits bracket information in the template editing form of FIG. 4.

FIG. 5B is a display diagram illustrating an exemplary view 70 that demonstrates how practitioner 8 edits bracket information in template editing form 66 (FIG. 4). In view 70, practitioner 8 may change the bracket height for a tooth or bring down a list of possible brackets available for the tooth. As illustrated in FIG. 5B, practitioner 8 may select no bracket by positioning a cursor over an item labeled "(None)".

Figure 5C:
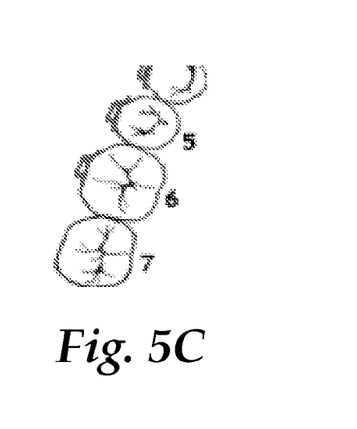
FIG. 5C is a display diagram illustrating an exemplary view detailing an arch graphic in the template editing form of FIG. 4.

FIG. 5C is a display diagram illustrating an exemplary view 72 detailing an arch graphic in template editing form 66 (FIG. 4). In particular, the arch graphic of view 72 shows only a portion of the arch in order to illustrate the presence or absence of a bracket. Notice the presence of brackets on teeth 5 and 6 and the absence of a bracket on tooth 7.

Figure 6:
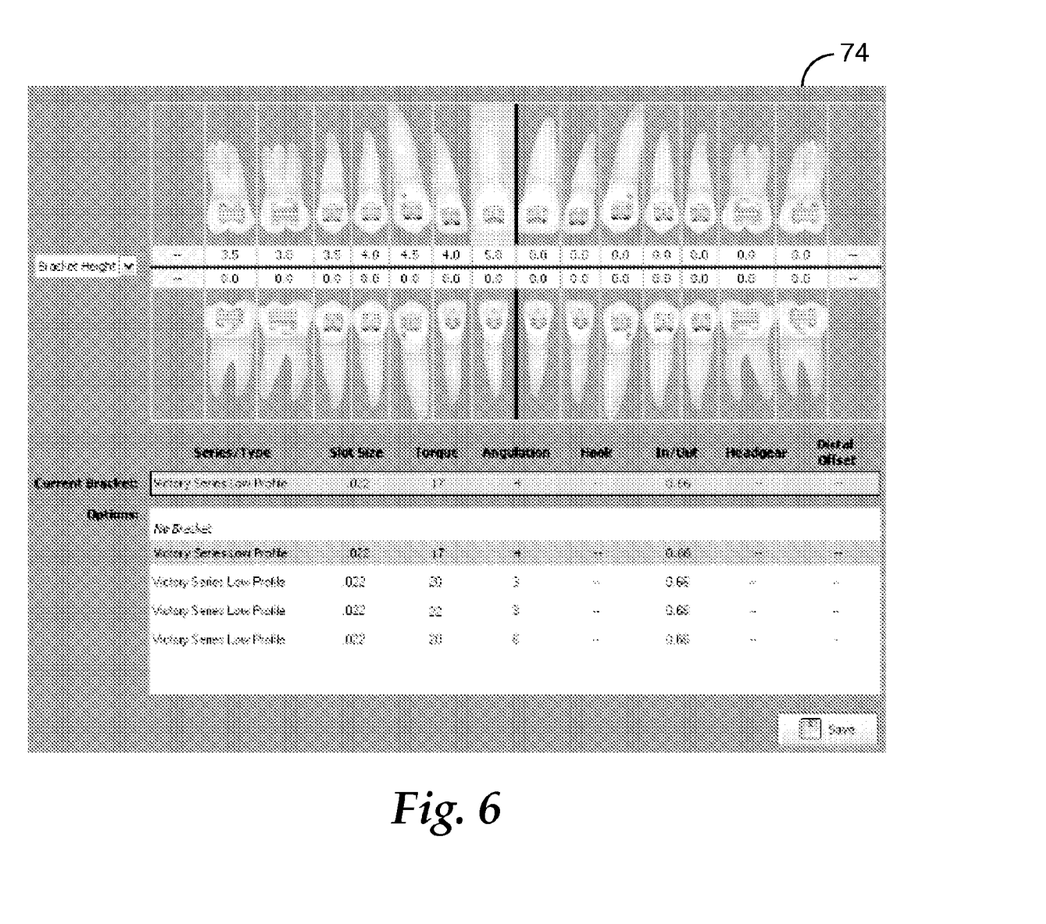
FIG. 6 is a display diagram illustrating an exemplary template editing form that arranges orthodontic prescription template information in a graphical tooth chart.

FIG. 6 is a display diagram illustrating an exemplary template editing form 74 that arranges orthodontic prescription template information in a graphical tooth chart. Template editing form 74 combines some of the features of template editing forms 50 and 66. Rather than showing all bracket attribute information at the same time, template editing form 74 provides graphical information for the most pertinent information and allows practitioner 8 to quickly browse through bracket information. In this way, template editing form 74 may allow practitioner 8 to view the most relevant information quickly.

Template editing form 74 displays a horizontal row of bracket attribute values for each tooth. In FIG. 6, the "Bracket Height" bracket attribute is displayed. To view other bracket attributes for a tooth, practitioner 8 may select the tooth from the graphic display of teeth. When practitioner 8 selects the tooth, bracket information and choices for that tooth appear below the graphic.

Figure 7A:
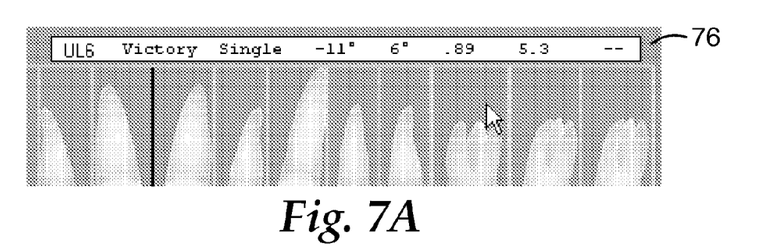
FIG. 7A is a display diagram illustrating an exemplary view that demonstrates a tool-tip display of bracket information within the template editing form of FIG. 6.

FIG. 7A is a display diagram illustrating an exemplary view 76 that demonstrates a tool-tip display of bracket information within template editing form 74 (FIG. 6). Unlike template editing forms 50 and 66, template editing form 74 does not display all bracket information at once. However, template editing form 74 may provide a tool-tip display for each tooth. The tool-tip display shows bracket information for a tooth when practitioner 8 positions a cursor over the tooth. By moving the cursor across a row of teeth, practitioner 8 may quickly browse through all of the bracket information while still displaying a full selection grid for a selected tooth.

Figure 7B:
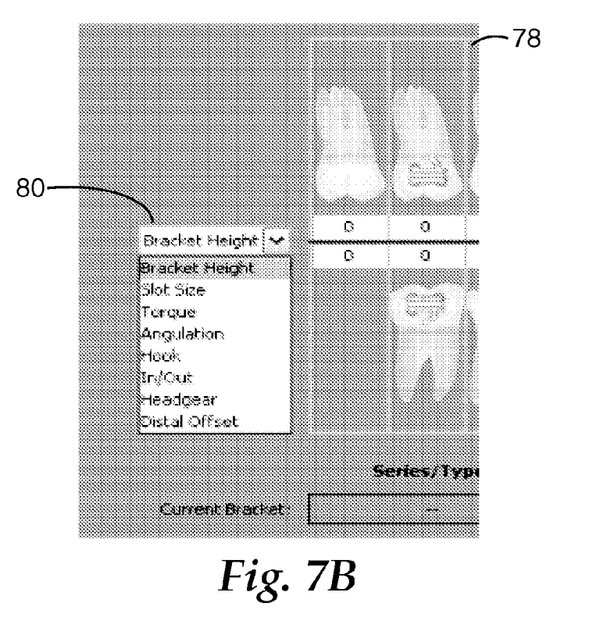
FIG. 7B is a display diagram illustrating an exemplary view that demonstrates a combo-box to select bracket information within template editing form of FIG. 6.

FIG. 7B is a display diagram illustrating an exemplary view 78 that demonstrates a combo-box 80 to select bracket information within template editing form 74 (FIG. 6). In view 78, practitioner 8 may select a bracket attribute from combo box 80. Combo box 80 contains a list of the different bracket attributes. When practitioner 8 selects a bracket attribute from combo box 80, template editing form 74 displays values of the bracket attribute for each tooth. Thus, practitioner 8 may view the value of any specific attribute across all teeth at the same time.

Figure 7C:
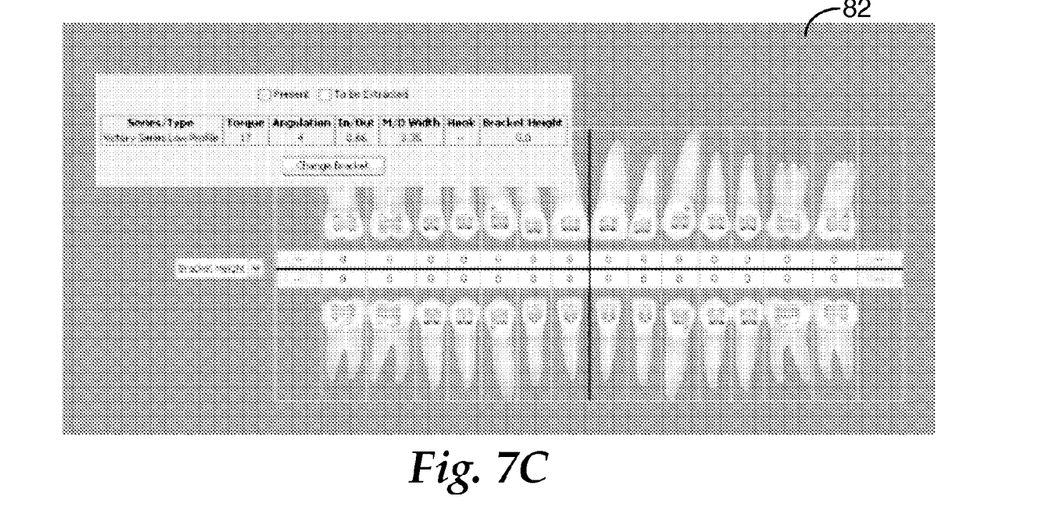
FIG. 7C is a display diagram illustrating an exemplary view that demonstrates a pop-up box that behaves similarly to a tool-tip and also includes bracket attributes and other controls.

FIG. 7C is a display diagram illustrating an exemplary view 82 that demonstrates a pop-up box that behaves similarly to a tool-tip and also includes bracket attributes and other controls. View 82 displays full bracket information for the selected tooth close to the tooth location. The pop-up box of view 82 may be a static display (i.e., a display that stays in place until the next tooth selection is made) or a tool-tip type of display where the values change as the cursor moves across the teeth.

For any of the graphical representations described above, the bracket pictures may be generic or specific, or they can be generic while conveying some specific information. In particular, in a generic bracket picture every bracket representation looks similar and does not convey any specific bracket type information. On the other hand, in a specific bracket picture every bracket representation shows a realistic view of the selected bracket, for example brackets from different product lines will look different. In other cases, the bracket pictures may be generic but have some specifics. In other words, the brackets are mostly generic but convey some attribute information for the bracket (e.g., showing whether a bracket has a hook or not, showing the degree of angulation accurately, etc).

Figure 8:
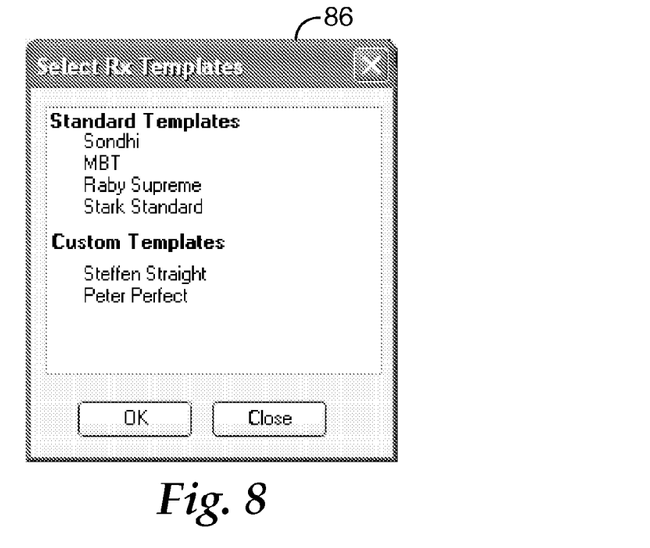
FIG. 8 is a display diagram illustrating an exemplary template selection view.

FIG. 8 is a display diagram illustrating an exemplary template selection view 86. Practitioner 8 may use template selection view 86 to select and retrieve one of templates 44 (FIG. 2). Note that template selection view 86 includes a list of standard templates 46 and custom templates 48.

Figure 9:
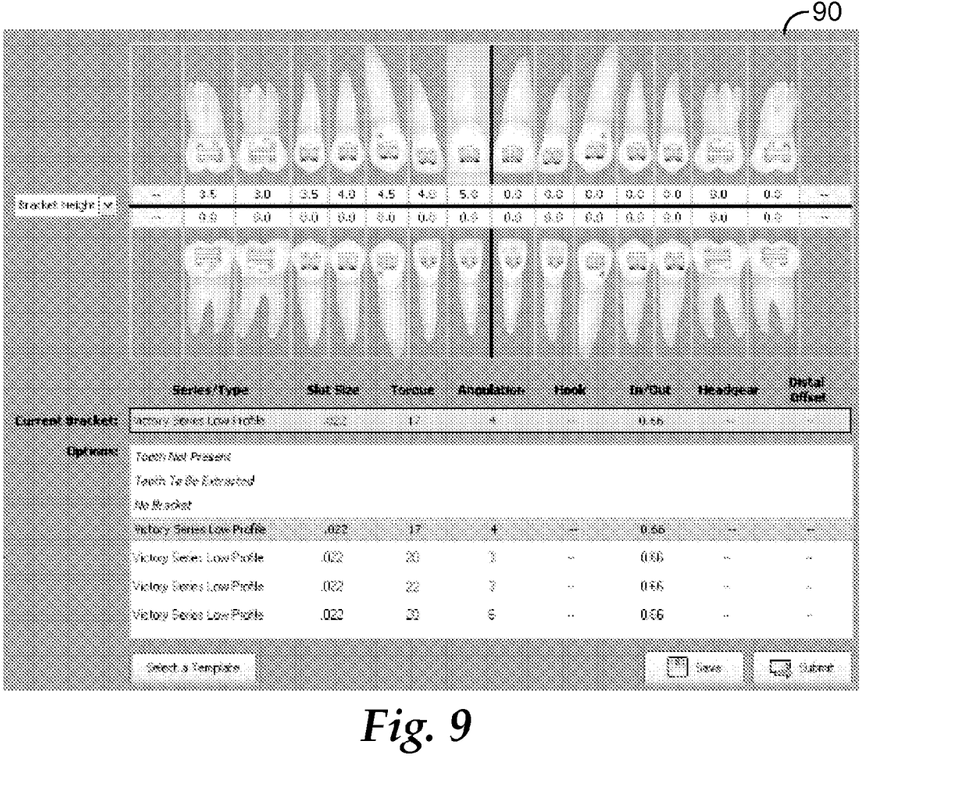
FIG. 9 is a display diagram illustrating an exemplary prescription form using a graphical tooth chart format similar to the template editing form of FIG. 6.

FIG. 9 is a display diagram illustrating an exemplary prescription form 90 using a graphical tooth chart format similar to template editing form 74 (FIG. 6).

Figure 10A:
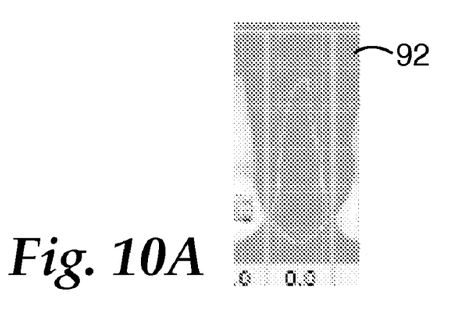
FIG. 10A is a display diagram illustrating an exemplary view displaying a missing tooth within the exemplary prescription form of FIG. 9.

FIG. 10A is a display diagram illustrating an exemplary view 92 displaying a missing tooth within exemplary prescription form 90 (FIG. 9).

Figure 10B:
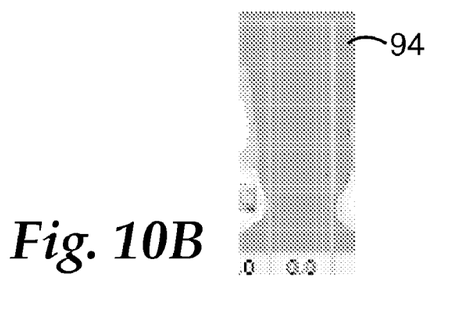
FIG. 10B is a display diagram illustrating an alternate exemplary view displaying a missing tooth within the exemplary prescription form of FIG. 9.

FIG. 10B is a display diagram illustrating an alternate exemplary view 94 displaying a missing tooth within exemplary prescription form 90 (FIG. 9).

Figure 10C:
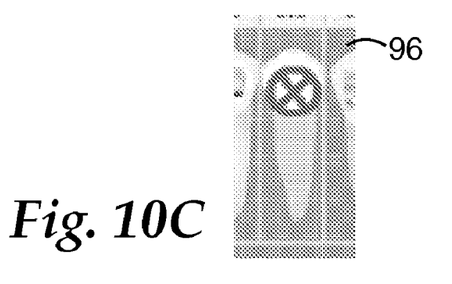
FIG. 10C is a display diagram illustrating an exemplary view displaying a tooth to be extracted within the exemplary prescription form of FIG. 9.

FIG. 10C is a display diagram illustrating an exemplary view 96 displaying a tooth to be extracted within exemplary prescription form 90 (FIG. 9).

Figure 10D:
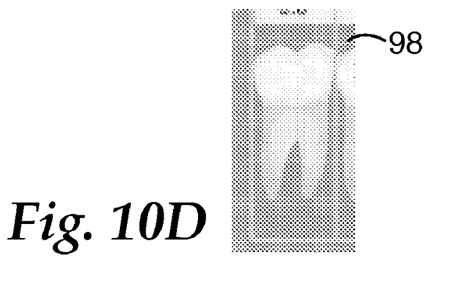
FIG. 10D is a display diagram illustrating an exemplary view displaying a tooth on which no bracket is to be placed within the exemplary prescription form of FIG. 9.

FIG. 10D is a display diagram illustrating an exemplary view 98 displaying a tooth on which no bracket is to be placed within exemplary prescription form 90 (FIG. 9).

FIG. 11 is a display diagram in which an exemplary prescription form 100 using a tooth chart with columnar bracket attributes similar to template editing form 50 (FIG. 3A). In prescription form 100 checkboxes within the columnar bracket attributes may represent whether a tooth is missing or whether a tooth is to be extracted.

Figure 12:
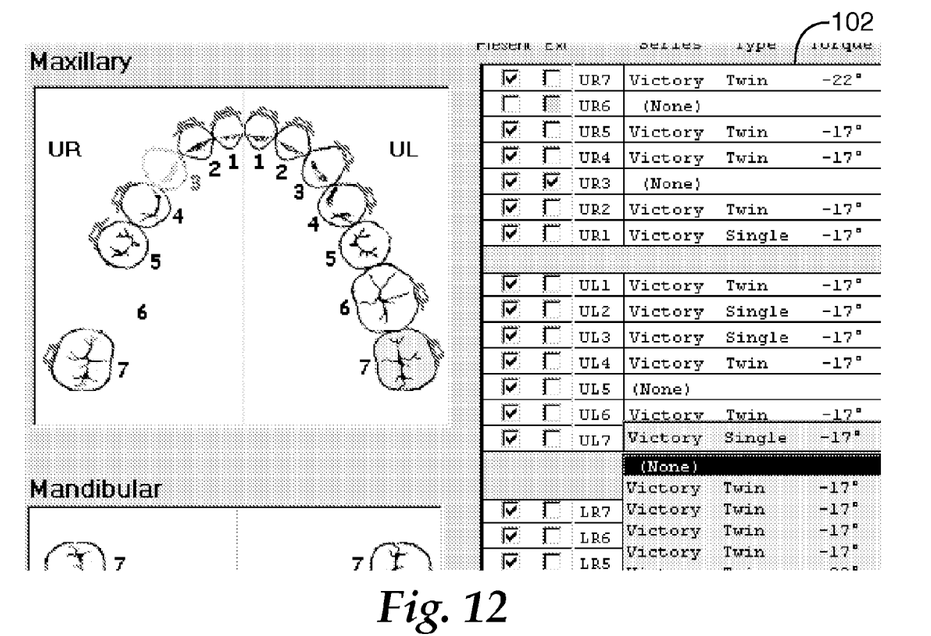
FIG. 12 is a display diagram in which an exemplary prescription form using a stacked quadrant format with arch graphics and row-based bracket attributes similar to the template editing form of FIG. 4.

FIG. 12 is a display diagram in which an exemplary prescription form 102 using a stacked quadrant format with arch graphics and row-based bracket attributes similar to template editing form 66 (FIG. 4).

Figure 13:
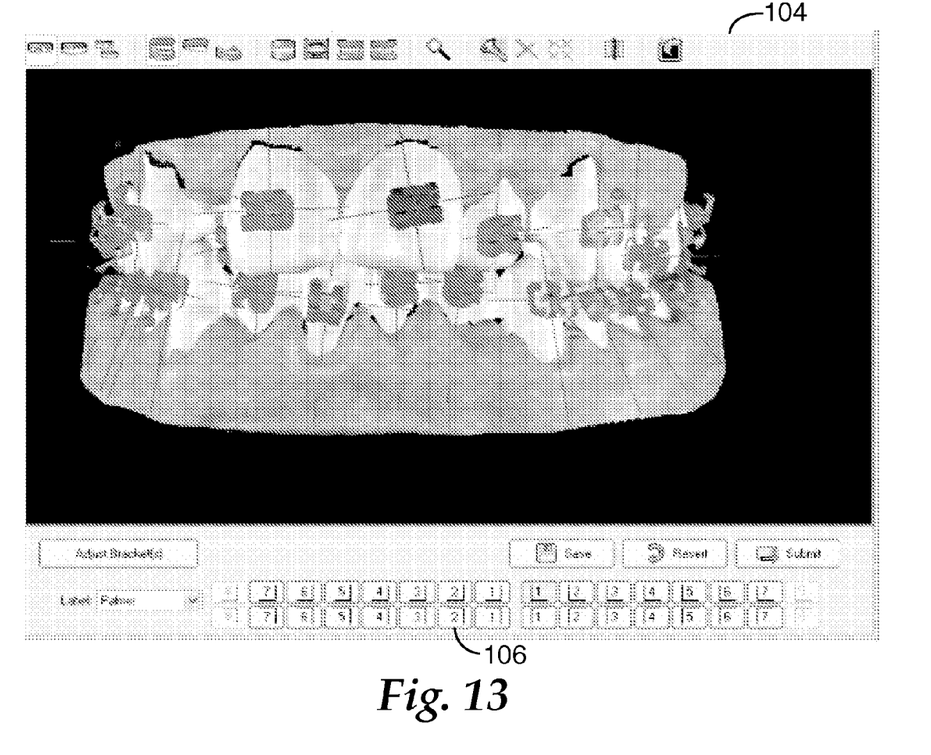
FIG. 13 is a display diagram illustrating an exemplary 3D dental model of the teeth of a patient with brackets that correspond to current bracket attribute values of an orthodontic prescription template.

FIG. 13 is a display diagram illustrating an exemplary 3D dental model 104 of the teeth of patient 6 with brackets that correspond to current bracket attribute values of an orthodontic prescription template. In addition, FIG. 13 includes tooth chart buttons 106 that correspond to tooth chart buttons in template editing format 50 (FIG. 3A). The layout of controls in FIG. 13 may assist in modeling tasks. For example, FIG. 13 shows bracket buttons arranged in the Tooth Chart Format on a toolbar-like panel and also uses a combo box to control which single attribute is currently displayed across the prescription. In FIG. 13, selecting a bracket in the toolbar causes the corresponding bracket to be selected in 3D model 104, (and vice versa).

Figure 14:
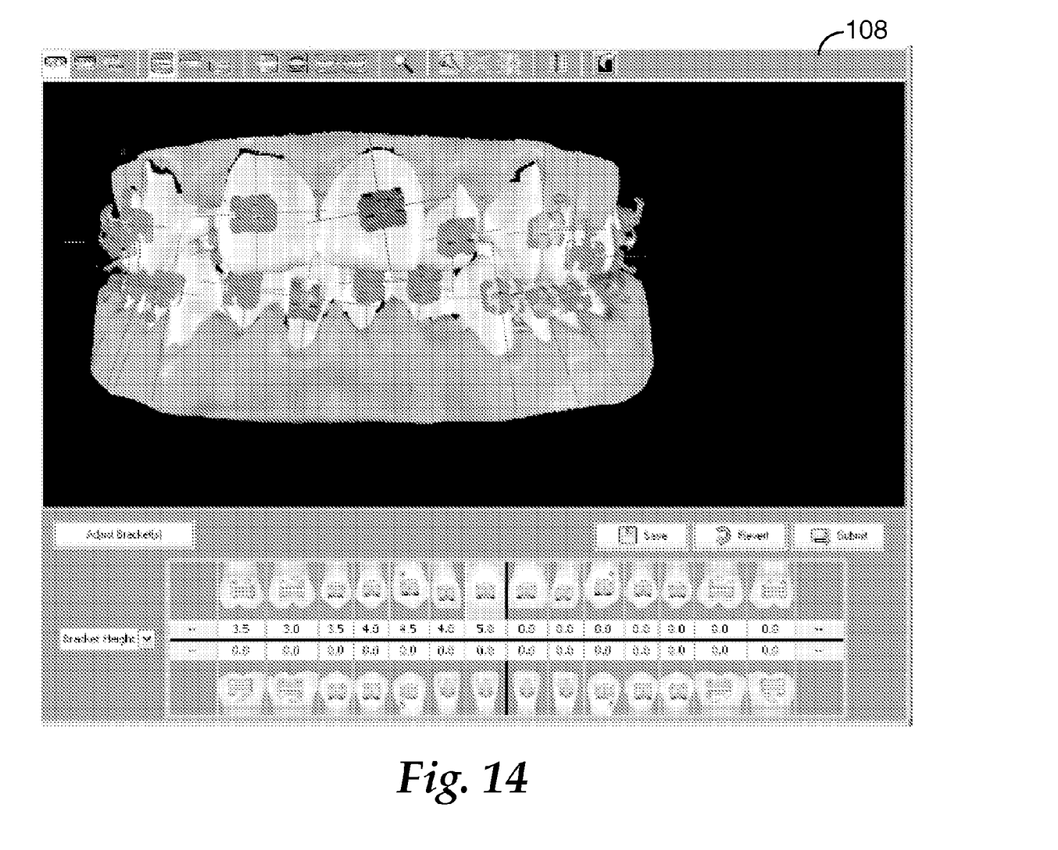
FIG. 14 is a display diagram illustrating an exemplary 3D dental model with a graphical tooth chart that corresponds to the graphical tooth chart in the template editing format of FIG. 6.

FIG. 14 is a display diagram illustrating an exemplary 3D dental model 106 with a graphical tooth chart that corresponds to the graphical tooth chart in template editing format 74 (FIG. 6). In FIGS. 13 and 14, the tooth charts function as bracket selection toolbars.

Various implementations and embodiments of the invention have been described. Nevertheless, it is understood that various modifications can be made without departing from the invention. These and other embodiments are within the scope of the following claims.

The invention claimed is:

1. A computer-based method comprising:
retrieving data representing an electronic orthodontic prescription template, wherein the orthodontic prescription template defines a plurality of default orthodontic appliances associated with teeth of a generic dental arch, wherein the orthodontic prescription template associates each of the default orthodontic appliances with a corresponding tooth of the generic dental arch, and wherein, for each of the default orthodontic appliances, the orthodontic prescription template specifies a default location and orientation of the appliance with respect to the corresponding tooth of the generic dental arch;
generating an orthodontic prescription that is specific to a patient's teeth by modifying the orthodontic prescription template with orthodontic modeling software to form the orthodontic prescription; and
displaying the orthodontic prescription and a virtual representation of the patient's teeth within a three-dimensional (3D) environment.

2. The method of claim 1, further comprising communicating the patient-specific orthodontic prescription via a computer network to a manufacturing facility that constructs an indirect bonding tray for use in physically placing brackets on the patient's teeth.

3. The method of claim 1,
wherein the appliances comprise brackets, and
wherein the electronic orthodontic prescription template is a custom template previously generated by modification of at least one attribute of a standard prescription template in response to input from an orthodontic practitioner, and
wherein generating an orthodontic prescription that is specific to a patient's teeth comprising further modifying the custom orthodontic prescription template with the orthodontic modeling software to form the patient-specific orthodontic prescription.

4. The method of claim 1, further comprising:
importing to a computer system an electronic orthodontic prescription template provided by a vendor, wherein the electronic orthodontic prescription template provided by the vendor includes data that defines the default orthodontic appliances as default virtual brackets and specifies, for each of the default virtual brackets, a default location and orientation of the default virtual bracket with respect to a corresponding tooth of the generic dental arch, and wherein electronic orthodontic prescription template specifies attributes for each of the default virtual brackets including an identification of the bracket by brand name; and
saving the imported orthodontic prescription template to a database of orthodontic prescription templates.

5. The method of claim 1, further comprising exporting the orthodontic prescription template from a first computer system to a second computer system providing a second 3D environment.

6. The method of claim 1, further comprising:
presenting a template editing form that displays the default orthodontic appliances the orthodontic prescription template and the default generic dental arch using a graphical user interface.

7. The method of claim 6, further comprising, in response to input from the user interacting with the template editing form, modifying the orthodontic prescription template to create a custom orthodontic template.

8. The method of claim 6,
wherein presenting a template editing form comprises displaying a tooth chart having a plurality of columns, each of the columns corresponding to a different tooth of the generic dental arch and listing bracket attributes of the default orthodontic appliance associated with the tooth of the generic dental arch, and
wherein the each of the columns is selectable and allows the user to modify the bracket attributes of the default orthodontic appliance to create a custom orthodontic prescription template.

9. The method of claim 6, further comprising displaying a prescription form separate from the template editing form, wherein the prescription form includes a three-dimensional (3D) model of the patient's teeth with brackets that correspond to current default orthodontic appliances and bracket attribute values specified by the orthodontic prescription template.

10. The method of claim 6, wherein displaying the orthodontic prescription comprises displaying arch graphics with row-based bracket attributes.

11. The method of claim 6, wherein displaying the orthodontic prescription comprises displaying a graphical tooth chart.

12. The method of claim 1, wherein generating an orthodontic prescription comprises:
using a graphical user interface to display the orthodontic prescription template and the virtual representation of the patient's teeth; and
manipulating bracket attributes displayed through the graphical user interface to create the orthodontic prescription that is specific to the patient's teeth.

13. The method of claim 1, wherein the template has ownership attributes that allow the template to be associated with a user.

14. A computing device comprising:
a database to store data defining an electronic orthodontic prescription template, wherein the orthodontic prescription template associates each of a plurality of default virtual orthodontic appliances with a corresponding tooth of a generic dental arch, and wherein, for each of the default virtual orthodontic appliances, the orthodontic prescription template specifies a default location and orientation of the default virtual orthodontic appliance with respect to the corresponding tooth of the generic dental arch;

a modeling software module to facilitate generation of an orthodontic prescription that is specific to a patient's teeth by modifying the template in response to input from a user to form a patient-specific orthodontic prescription; and
a user interface to display the patient-specific orthodontic prescription and a virtual representation of the patient's teeth within a three-dimensional (3D) environment,
wherein the user interface comprises:
a template editing form displaying a tooth chart of the generic dental arch and listing bracket attributes of the default orthodontic appliances associated with the teeth of the generic dental arch, wherein the template editing form allows the user to modify the bracket attributes of the default orthodontic appliances to create a custom orthodontic prescription template for the generic dental arch; and
a prescription form displaying a 3D model of the patient's teeth with brackets that correspond to the default orthodontic appliances and bracket attribute values specified by the custom orthodontic prescription template for the generic dental arch, wherein the prescription form allows the user to further modify the brackets and bracket attribute values to create the patient-specific orthodontic prescription.

15. The computing device of claim 14, further comprising a network interface to communicate the patient-specific orthodontic prescription to a manufacturing facility that constructs an indirect bonding tray for use in physically placing brackets on the patient's teeth.

16. The computing device of claim 14, wherein the template is a custom template.

17. The computing device of claim 14, wherein the orthodontic prescription template is imported into the database.

18. The computing device of claim 14, wherein the orthodontic prescription template is exportable.

19. The computing device of claim 14, wherein the modeling software module comprises a graphical user interface to display the orthodontic prescription template.

20. The computing device of claim 19, wherein a user edits the orthodontic prescription template using the graphical user interface.

21. The computing device of claim 19, wherein the graphical user interface comprises a tooth chart with columnar bracket attributes.

22. The computing device of claim 19, wherein the graphical user interface comprises a three-dimensional (3D) model of the patient's teeth with brackets that correspond to current bracket attribute values of the orthodontic prescription template.

23. The computing device of claim 19, wherein the graphical user interface comprises arch graphics with row-based bracket attributes.

24. The computing device of claim 19, wherein the graphical user interface comprises a graphical tooth chart.

25. The computing device of claim 14, wherein the template has ownership attributes that allow the template to be associated with a user.

* * * * *